United States Patent [19]

Åkerfeldt

[11] Patent Number: 5,542,427
[45] Date of Patent: Aug. 6, 1996

[54] DEVICE FOR STERILE PACKAGING OF MEDICAL EQUIPMENT

[75] Inventor: Dan Åkerfeldt, Uppsala, Sweden

[73] Assignee: Radi Medical Systems, Uppsala, Sweden

[21] Appl. No.: 272,742

[22] Filed: Jul. 11, 1994

Related U.S. Application Data

[63] Continuation of Ser. No. 27,900, Mar. 8, 1993, abandoned, and a continuation of Ser. No. 712,413, Jun. 10, 1991, Pat. No. 5,307,811.

[30] Foreign Application Priority Data

| Jun. 11, 1990 | [SE] | Sweden | 9002077 |
| Oct. 12, 1990 | [SE] | Sweden | 9003271 |
| Aug. 28, 1992 | [SE] | Sweden | 9202484 |

[51] Int. Cl.⁶ ........................... A61B 5/02
[52] U.S. Cl. ............... 128/677; 128/668; 606/157
[58] Field of Search ............... 606/157, 158, 606/192, 195, 201, 202, 203, 204; 602/13; 128/672, 677, 668, 637, 845, 846, 869

[56] References Cited

U.S. PATENT DOCUMENTS

| 3,625,219 | 12/1971 | Abrams | 606/203 |
| 3,756,239 | 9/1973 | Smythe | 606/202 |
| 3,779,249 | 12/1973 | Semler | 606/201 |
| 3,874,042 | 4/1975 | Eddleman et al. | 606/157 X |
| 3,874,387 | 4/1975 | Barbieri | 606/201 X |
| 3,884,240 | 5/1975 | Gilman | 606/201 |
| 4,175,562 | 11/1979 | Honan | 606/202 |
| 4,224,945 | 9/1980 | Cohen | 602/202 X |
| 4,233,980 | 11/1980 | McRae et al. | 606/201 |
| 4,246,893 | 1/1981 | Berson | 606/195 X |
| 4,957,105 | 9/1990 | Kurth | 606/203 X |

FOREIGN PATENT DOCUMENTS

| 2664807 | 1/1992 | France | 606/201 |

Primary Examiner—Sam Rimell
Attorney, Agent, or Firm—Foley & Lardner

[57] ABSTRACT

The present invention relates to a sterile packaging which considerably reduces the risk of contamination of a part which is in contact with an area on a patient's body, and which can be exposed to the risk of infection. More specifically, the invention has a replaceable air cushion unit for use in conjunction with a femoral compressor, which includes a base plate, an inflatable air cushion having a periphery attached to the base plate and a shielding element covering and sealing the air cushion from ambient surroundings. The base plate is also detachable from the femoral compressor after use.

23 Claims, 3 Drawing Sheets

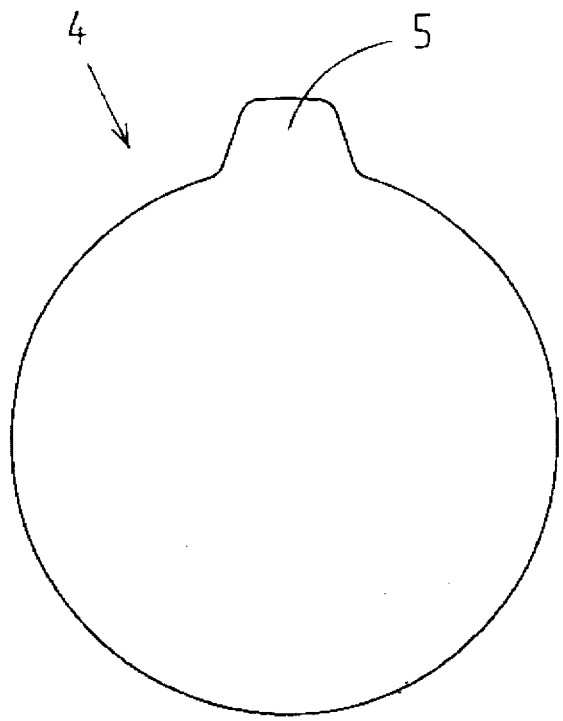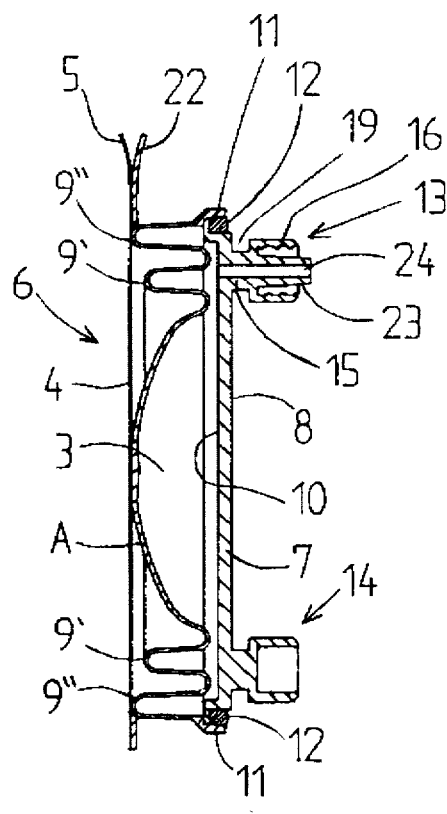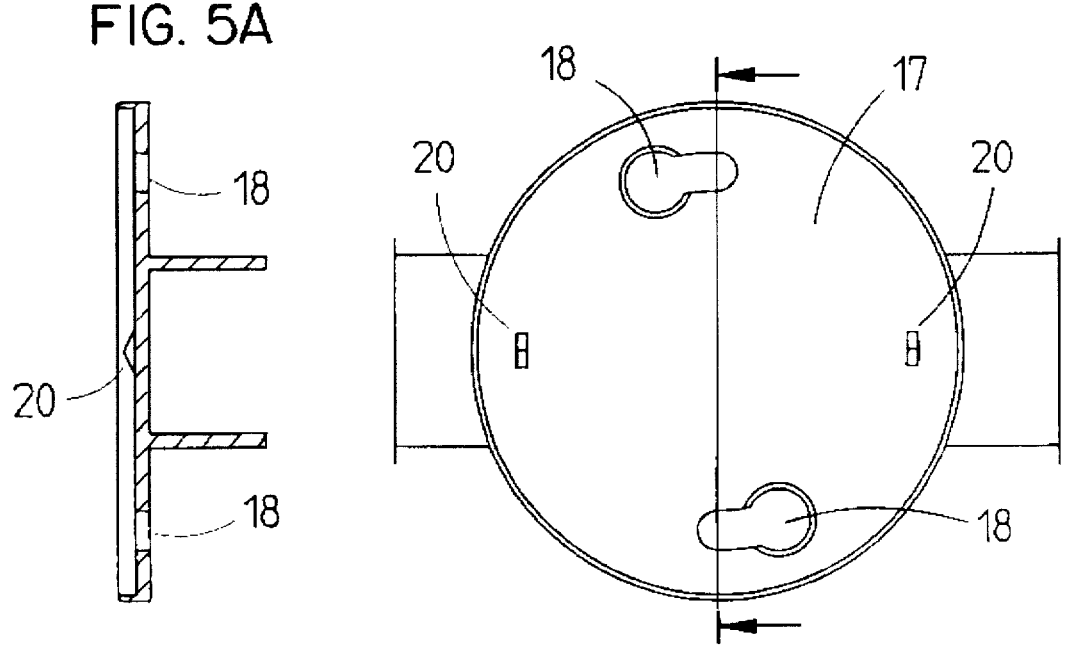

DEVICE FOR STERILE PACKAGING OF MEDICAL EQUIPMENT

This application is a continuation of application Ser. No. 08/027,900, filed Mar. 8, 1993, and a continuation of application Ser. No. 07/712,413, now U.S. Pat. No. 5,307,811.

BACKGROUND OF THE INVENTION

The present invention relates to sterile packaging of medical equipment, and in particular to a device for the simplification of manual handling of parts which must be sterile when placed in contact with an area on the body of a patient, for example, a puncture site or the like.

The invention is especially suitable for use with inflatable cushions which are used for femoral compression by means of a femoral compressor as described in Swedish patent application nos. 9002077-7 and 9003271-5, which are herein incorporated by reference.

In Swedish patent application nos. 9002077-7 and 9003271-5 the femoral compressor is supplied as one unit (arch and air cushion) in a sterile package which is opened just prior to application onto the patient. The disadvantage with this construction is that the manufacturing and transport costs are high, and that the waste, i.e. the entire unit, is bulky. For possible reuse, the entire compressor must be resterilized, in e.g. an autoclave, in which case the device's large volume is a disadvantage.

The greatest disadvantage with the femoral compressors of the cited application is that there is a risk that the contact surface of the permanently mounted air cushion may be contaminated between the time that the sterile compressor is removed from the package and when it is applied, e.g. on the bleeding puncture site.

In addition, the blood contamination of the compressor must be treated as hazardous waste, resulting in troublesome handling of the bulky unit.

In an alternative form of the compression unit of Swedish patent application nos. 9002077-7 and 9003271-5, the air cushion is a separate part and is mounted on a base plate 7 which is attached to the arch 2 by means of e.g. double adhesive tape.

Even in this case, there is a risk of contaminating the air cushion when attaching it to the arch, since the sterile packaging enclosing the cushion and its base plate must be opened before the cushion is mounted manually onto the arch.

In general, sterile, single-use items which are used in health care and especially during surgical procedures, are usually packaged in sealed, gas-permeable pouches (e.g. TYVEK, a du Pont trademark), so that they can be gas sterilized using ethylene oxide gas after the pouches have been sealed. Sterilization of the sealed item can also be done by means of radiation treatment (electron radiation, that is, beta sterilization or gamma radiation). A disadvantage with this kind of sterile packaging is that when the part is to be used, it must be removed from the pouch and handled manually, which clearly implies a risk of contamination of the part on the way to the patient, even if the distance is not very great.

Therefore, there is a need to be able to handle a sterile part in a safe way, so that the risk for contamination is reduced as much as possible. This can be done by using a package which is constructed in such a way that the seal need not be broken until just before the part is placed on the patient. In this way, the part, e.g. an air cushion for a femoral compressor, can be handled manually and positioned on the patient with no particular care being necessary to avoid contamination.

SUMMARY OF THE INVENTION

The object of the present invention is therefore to provide a sterile package which considerably reduces the risk of contamination of a part which shall be brought into contact with an area on the patient's body, and which can be exposed to the risk of infection.

According to one aspect of the present invention, there has been provided a replaceable air cushion unit for use in conjunction with a femoral compressor, comprising a base plate which is detachable from the femoral compressor, and an inflatable air cushion having a periphery attached to the base plate. The replaceable unit further includes a shielding element covering and sealing the air cushion from ambient surroundings.

In accordance with another aspect of the present invention, there has been provided a method of removably attaching an air cushion unit to a femoral compressor, comprising the steps of attaching an air cushion to the base plate, attaching the base plate to the femoral compressor, and detaching the base plate from the femoral compressor after use. The method of removably attaching the air cushion may further comprise the steps of sealing the air cushion from ambient surroundings by covering the air cushion with a sealing element and detaching the base plate from the femoral compressor after use.

Since the present invention is constructed in such a way that the seal need not be broken until just before the part is placed on the patient, the air cushion can be handled manually and positioned on the patient with no particular care being necessary to avoid contamination.

Further objects, features and advantages will become apparent from the detailed description of exemplary embodiments which follows, when considered with the drawings.

BRIEF DESCRIPTION OF THE DRAWINGS

A detailed description of the preferred embodiments of the invention will be given below as applied to a femoral compressor according to Swedish patent application nos. 9002077-7 and 9003271-5, and with reference to the attached drawings in which:

FIG. 3 shows a sterile lid constructed in accordance with the invention;

FIG. 4 shows an air cushion belonging to the femoral compressor in FIG. 1, with a sterile lid according to the invention;

FIG. 5A shows in cross-section, and FIG. 5B from below, a part of the compression arch in FIG. 2 adapted to rest against the base plate of a replaceable air cushion;

DETAILED DESCRIPTION OF THE PREFERRED EMBODIMENTS

Figure 1:
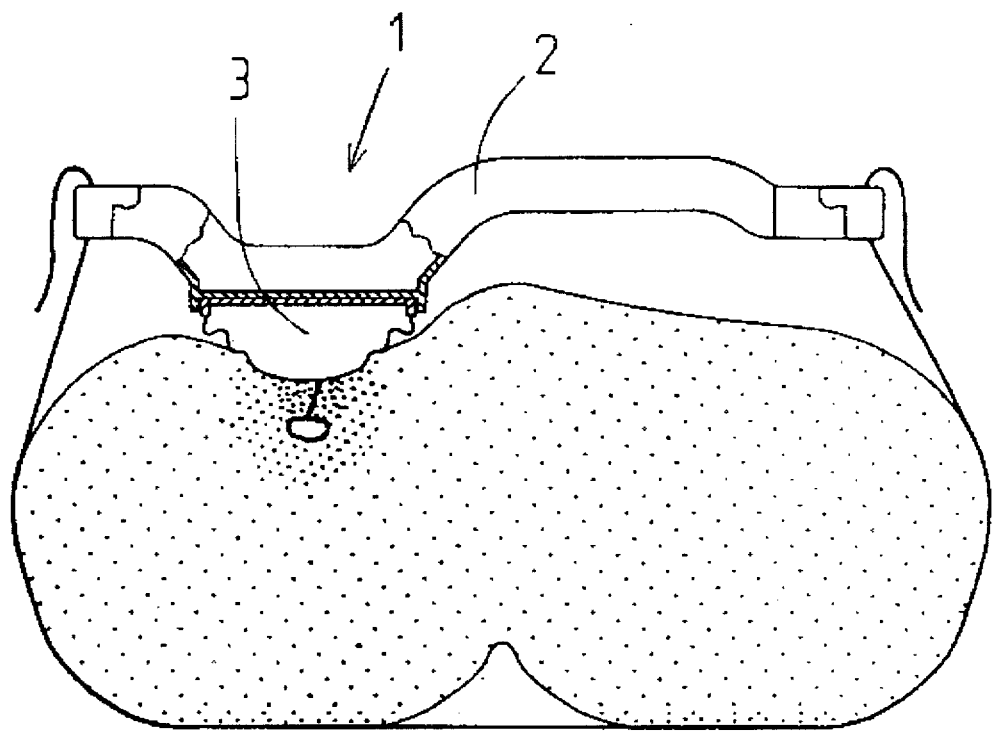
FIG. 1 shows a cross-section of a patient with a femoral compressor of the above-mentioned type in position over a puncture site.
Figure 2:
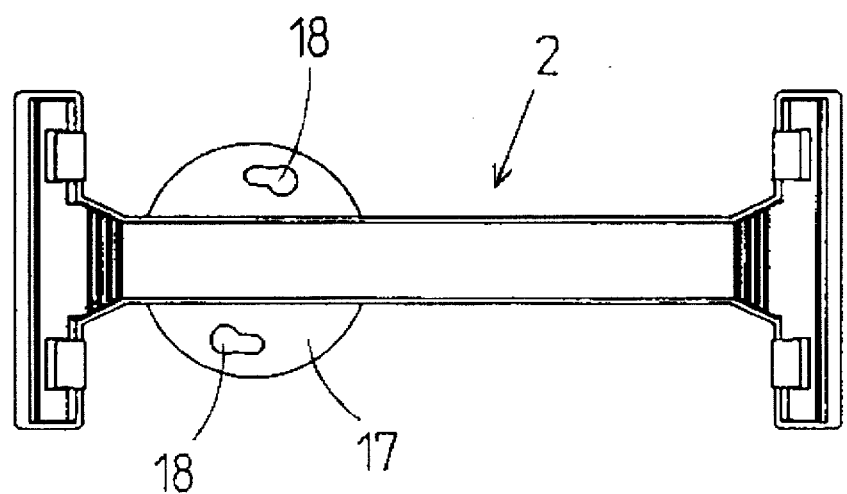
FIG. 2 shows a compression arch belonging to the femoral compressor in FIG. 1.
Figure 6B:
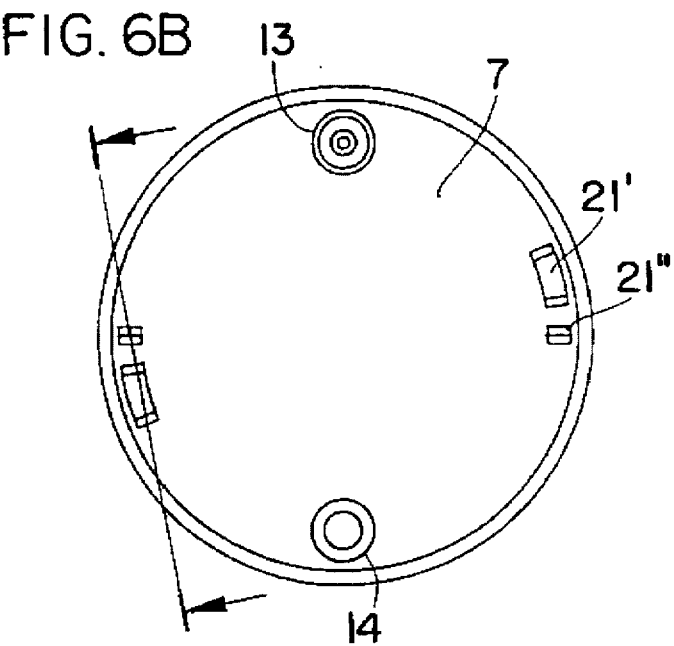
FIG. 6A shows the base plate in cross-section and FIG. 6B from below.
Figure 6A:
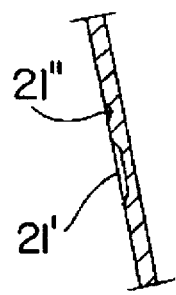
Figure 7:
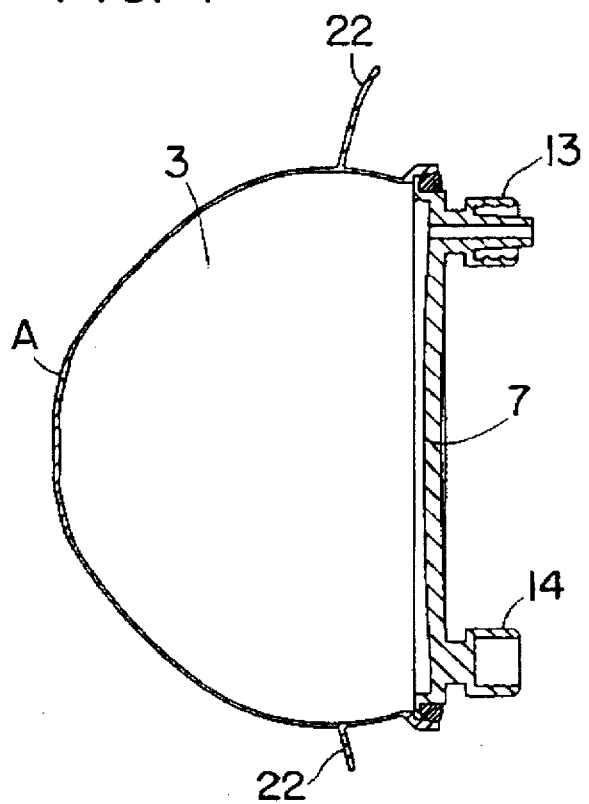
FIG. 7 shows the air cushion unit in an inflated state.

The femoral compressor 1 shown in FIG. 1 consists of an arch 2 to which an inflatable air cushion 3 is permanently attached. This arch 3 is applied to the puncture site in the femoral artery in order to stop bleeding and is inflated to a suitable pressure using, for example, a manual inflator. Therefore, there is a risk of infection if the air cushion should be contaminated with infectious material.

In Swedish patent application nos. 9002077-7 and 9003271-5 the femoral compressor is supplied as one unit (arch and air cushion) in a sterile package which is opened just prior to application onto the patient. The disadvantage with this construction is that the manufacturing and transport costs are high, and that the waste, i.e. the entire unit, is bulky. For possible reuse, the entire compressor must be resterilized, in e.g. an autoclave, in which case the device's large volume is a disadvantage.

FIG. 3 of the present application shows a shielding element in the form of a sterile lid 4 according to the present invention, intended to be used for sealing the air cushion 3 which is part of the air cushion unit 6 (described below). The lid provides a protective element 4, and includes a primary base layer of spray fiber material (spun bonded), or of a gas permeable, or non-gas permeable polymer material, and a second layer of e.g. melt-glue or of a plastic material which is meltable, so that element 4 is fusible with the above-mentioned periphery.

A suitable, commercially available material for the lid is TYVEK (registered trademark of du Pont).

As seen in FIG. 4, a replaceable air cushion unit, single use in nature, is generally shown with the reference number 6, and includes a base plate 7, an upper side 8 of which is applied to the femoral compressor's arch 2. This application is done by means of a "snap attachment" which will be described in detail below. The attachment comprises notches 18 on one of the plates 7, 17 and connecting elements 13, 14 on the other plate 17, 7 insertable in the notches such that a snap or locking fit is obtained.

On the base plate there is an inflatable air cushion 3 which is mounted by gluing or fusing along the base plate's 7 periphery. The material which the cushion is made of seen from a cross sectional view, folded at 9', 9" so that the air cushion when not inflated, that is, as it is packaged, takes up as little volume as possible.

Along the periphery of the base plate is a groove 11; a melt-glue 12 is placed in the groove and subjected to a heat and pressure treatment well known to the skilled artisan, which establishes an airtight sealing of the air cushion 3 against the base plate 7. A pair of attachment elements 13, 14 stick out from the upper side 8 of the plate 7. The attachment elements 13, 14 are designed so that an end 15 which connects to the base plate 7 is smaller in diameter than an end 16 which is not connected to the baseplate 7. A web or waist 19 is therefore formed between the baseplate and the thicker end piece 16.

As illustrated in FIG. 5, the thicker ends 16 of attachment elements 13 and 14 are designed to fit precisely into a pair of notches 18 of connecting part 17, referred to herein as a "locking fit". These notches have a narrower part 18' which stretches mainly along a line concentric with the periphery, and has a width equivalent in diameter to the narrower parts 15 of the connecting elements 13, 14. Furthermore, the thickness of connecting part 17 corresponds to the length of a waist 19. Therefore, if the replaceable air cushion unit's connecting element is fit into the arch's notches 18 and thereafter turned clockwise, then base plate 7 will fit tightly against the connecting part 17.

Furthermore, connecting part 17 is equipped with a protruding element 20, which "snaps" into corresponding notches 21" in base plate 7 when cushion part 6 is twisted into place. Thus unit 6 is locked onto arch 2 and is prevented from becoming loosened from it. In the illustrated embodiment, the protruding elements 20 are triangular. On the base plate, there are also notches 21' into which the element 20 slides when the air cushion unit 6 is initially placed against the connecting part 17 and the attachment elements 13 and 14 are fit into the larger (wider) part of the notches 18. When the unit 6 is then twisted into place, the element 20 is moved over the part between the notches 21' and 21", whereby the baseplate 7 gives somewhat. Thereafter, the element 20 falls into place in the notches 21" and thereby a locked position is reached and the desired "snap attachment" is achieved.

Alternatively, the protruding element 20 can be attached to the base plate 7, and the notches 21' and 21" can be attached to the connecting part 17.

One of the connecting elements 13 is designed so that it forms an attachment of LUER-LOCK type 23. There is a hole 24 in connecting element 13 through which air can be pumped in order to inflate air cushion 3 after the femoral compressor 1 has been placed on a patient. The base plate 7 can alternatively be attached to the femoral compressor 2 by double adhesive tape.

In order to ensure that the risk of contaminating the contact surface A of air cushion 3 is reduced as much as possible, it is suggested according to the present invention, that a lid (see FIG. 4), preferably made of a "spun bonded" material (spray fiber material), (e.g. TYVEC from du Pont) equipped with a melt-glue layer, or a layer of other material which can be melted so that a seal is formed, is attached to the air cushion 4. As seen in FIG. 3, the lid 4 is fused or glued along the periphery of the uninflated cushion 3. The fusing is done by using heat and pressure, typically approximately 130° C. and 400 kPa. The fusing time is typically approximately 2 s. The desired peel force should be 0.17–0.47N/mm (4.5–12N/inches), preferably 0.31N/mm (8N/inch), which is a suitable balance between good strength and unintentional opening and ease of opening the lid by hand. The lid is equipped with a tab 5 which makes it easy to remove the lid from the edge. The stripping force is typically 0.31N/mm (8N/inch).

After the lid 4 has been attached, the air cushion unit 6 can be sterilized by various means such as radiation with high energy radiation or by gas sterilization.

When using a femoral compressor with replaceable air cushion unit 6 of the type described, the air cushion unit 6 is first mounted onto the arch 2. Thanks to the lid 4 which protects the contact surface A on air cushion 3, the nurse or physician who applies the compressor to the patient does not need to be as careful, with regard to the manual handling of the entire instrument, as with the devices of Swedish patent application nos. 9002077-7 and 9003271-5. The unit 6 is mounted by putting the attachment elements 13, 14 into the notches 18, whereupon the unit is turned clockwise until it "snaps" into place thanks to the protruding elements' 20 working together with the notches 21 in connecting part 17. The femoral compressor 1 can now be taken to the patient, and immediately before application, the lid 4 is easily torn off by gripping the tab 5 and pulling diametrically over the air cushion. The stripping force is slight enough that this shall not cause any difficulties.

After satisfactory compression, that is when bleeding no longer occurs, the compressor is removed and the single-use air cushion unit 6 is disassembled by turning it counter-clockwise and pulling it out from the notches 18, whereupon it is discarded as waste. To avoid touching the blood-contaminated air cushion, the unit 6 can be loosened from the arch by turning the air cushion unit from behind using the protruding attachment elements 13 and 14.

While the devices herein described constitute preferred embodiments of the invention, it is to be understood that the invention is not limited to these precise devices, and that changes may be implemented without departing from the scope of the invention.

What is claimed is:

1. A replaceable air cushion unit for use in conjunction with a femoral compressor comprising:
   a) a base plate;
   b) an inflatable air cushion having a periphery attached to the base plate, and an inflation opening; and
   c) a shielding element covering and sealing the air cushion from ambient surroundings,
   wherein the shielding element is flexible and is attached to the periphery of the air cushion, and
   wherein the shielding element comprises a primary layer and a secondary layer, the secondary layer being meltable whereby the shielding element is fused to the periphery of the air cushion.

2. The air cushion unit of claim 1 wherein the shielding element has a gripping tab for easy removal of the shielding element from the air cushion.

3. The air cushion unit of claim 1 including a lip along an edge of the air cushion where the shielding element is attached.

4. The air cushion unit of claim 1 wherein the primary layer comprises spray fiber or polymer material.

5. The air cushion unit of claim 1 wherein the secondary layer when fused to the periphery of the air cushion requires a stripping force of 0.17–0.47N/mm (4.5–12N/inch).

6. The air cushion unit of claim 5 wherein the stripping force is approximately 0.31N/mm (8N/inch).

7. A replaceable air cushion unit on a femoral compressor comprising:
   a) a base plate;
   b) an inflatable air cushion having a periphery attached to the base plate, and an inflation opening;
   c) a shielding element covering and sealing the air cushion from ambient surroundings,
   wherein the shielding element is flexible and is attached to the periphery of the air cushion; and
   wherein the shielding element comprises a primary layer and a secondary layer, the secondary layer being meltable whereby the shielding element is fused to the periphery of the air cushion; and
   d) a femoral compressor in the shape of an arch, attachable to the base plate.

8. The method of removably attaching an air cushion unit to a femoral compressor, comprising the steps of:
   sealing an air cushion from ambient surroundings by covering the air cushion with a shielding element;
   attaching the air cushion to a base plate;
   attaching the base plate to the femoral compressor prior to use;.
   removing the shielding element prior to use; and
   detaching the base plate from the femoral compressor after use.

9. The method of claim 8 further comprising the step of sterilizing the air cushion.

10. The method of claim 9 performing the sterilization subsequent to covering the air cushion with the shielding element.

11. A replaceable air cushion unit for use in conjunction with a femoral compressor, comprising:
    a) a base plate which is adapted to attach to a femoral compressor;
    b) an inflatable air cushion having a periphery attached to the base plate, and an inflation opening; and
    c) locking fit notch means formed in the base plate, for receiving connecting elements on a connecting plate on the femoral compressor such that a locking fit is obtained,
    d) wherein said each of said locking fit notch means has a diameter, and has a part which extends generally along a line concentric with the periphery of the base plate, and said part has a width narrower than said diameter.

12. The air cushion unit of claim 11, further comprising protruding element means on the base plate, for inserting into snap fit notch means in a connecting plate on the femoral compressor such that a snap fit is obtained.

13. The air cushion unit of claim 11, further comprising snap fit notch means on the base plate, for receiving protruding elements on a connecting plate on the femoral compressor such that a snap fit is obtained.

14. A replaceable air cushion unit for use in conjunction with a femoral compressor, comprising:
    a) a base plate which is adapted to attach to a femoral compressor;
    b) an inflatable air cushion having a periphery attached to the base plate, and an inflation opening; and
    c) connecting element means unitary with the base plate, formed for inserting into locking fit notches in a connecting plate on the femoral compressor such that a locking fit is obtained.

15. The air cushion unit of claim 14, wherein each of said connecting element means has a diameter, and has a waist adjacent to said base plate, and said waist has a width narrower than said diameter.

16. The air cushion unit of claim 14, further comprising protruding element means on the base plate, for inserting into snap fit notches in a connecting plate on the femoral compressor such that a snap fit is obtained.

17. The air cushion unit of claim 14, further comprising snap fit notch means on the base plate, for receiving protruding element means on a connecting plate on the femoral compressor such that a snap fit is obtained.

18. A replaceable air cushion unit for use in conjunction with a femoral compressor comprising:
    a) a base plate which is adapted to attach to a femoral compressor;
    b) an inflatable air cushion having a periphery attached to the base plate, and an inflation opening; and
    c) double-adhesive tape on a side of the base plate opposite to the air cushion, wherein the base plate is attachable to a connecting plate on a femoral compressor.

19. The air cushion unit of claim 1, including double-adhesive tape on a side of the base plate opposite to the air cushion, wherein the base plate is attachable to a connecting plate on a femoral compressor.

20. The air cushion unit of claim 1, including locking fit notch means formed in the base plate, for receiving connecting elements on a connecting plate on the femoral compressor such that a locking fit is obtained, and each of said locking fit notch means has a diameter, and has a part which extends generally along a line concentric with the periphery of the base plate, and said part has a width narrower than said diameter.

21. The air cushion unit of claim 1, including connecting element means on the base plate, for inserting into locking fit notches in a connecting plate on the femoral compressor such that a locking fit is obtained, and each of said connecting element means has a diameter, and has a waist adjacent to said base plate, and said waist has a width narrower than said diameter.

22. The air cushion unit of claim 1, including triangular protruding element on the base plate, for inserting into snap fit notches in a connecting plate on the femoral compressor such that a snap fit is obtained.

23. The air cushion unit of claim 1, including triangular snap fit notch means in the base plate, for receiving triangular protruding elements on a connecting plate on the femoral compressor such that a snap fit is obtained.

* * * * *